(12) United States Patent
Frugier

(10) Patent No.: US 10,328,193 B2
(45) Date of Patent: Jun. 25, 2019

(54) EXTRACORPOREAL BLOOD TREATMENT APPARATUS WITH MULTIPLE TREATMENT SOLUTION RESERVOIRS

(71) Applicant: GAMBRO LUNDIA AB, Lund (SE)

(72) Inventor: Alain Frugier, Chazay d'Azergues (FR)

(73) Assignee: Gambro Lundia AB, Lund (SE)

( * ) Notice: Subject to any disclaimer, the term of this patent is extended or adjusted under 35 U.S.C. 154(b) by 207 days.

(21) Appl. No.: 13/786,618

(22) Filed: Mar. 6, 2013

(65) Prior Publication Data
US 2013/0248446 A1   Sep. 26, 2013

Related U.S. Application Data

(60) Provisional application No. 61/613,584, filed on Mar. 21, 2012.

(51) Int. Cl.
*A61M 1/16* (2006.01)
*A61M 1/36* (2006.01)

(52) U.S. Cl.
CPC ........ *A61M 1/3627* (2013.01); *A61M 1/1656* (2013.01); *A61M 1/1668* (2014.02)

(58) Field of Classification Search
None
See application file for complete search history.

(56) References Cited

U.S. PATENT DOCUMENTS

| | | |
|---|---|---|
| 3,677,242 A | 7/1972 | Shaye |
| 4,004,587 A | 1/1977 | Jess |
| 4,013,072 A | 3/1977 | Jess |
| 4,031,891 A | 6/1977 | Jess |
| 4,116,646 A | 9/1978 | Edwards |
| 4,208,193 A | 6/1980 | Munish |
| 4,262,668 A | 4/1981 | Schmidt |
| 4,278,084 A | 7/1981 | Pope, Jr. |
| 4,284,505 A | 8/1981 | Pope, Jr. |
| 4,340,479 A | 7/1982 | Pall |
| 4,431,545 A | 2/1984 | Pall |
| 4,459,139 A | 7/1984 | Von Reis |
| 4,521,212 A | 6/1985 | Ruschke |
| 4,615,694 A | 10/1986 | Raines |
| 4,617,124 A | 10/1986 | Pall |
| 4,906,260 A | 3/1990 | Emheiser |
| 4,908,019 A * | 3/1990 | Urquhart ............ A61M 5/1407 604/85 |

(Continued)

FOREIGN PATENT DOCUMENTS

EP   0 099 699 B1   2/1984
EP   0 081 655 A1   9/1985
(Continued)

*Primary Examiner* — Vickie Y Kim
*Assistant Examiner* — Bradley R Spies
(74) *Attorney, Agent, or Firm* — Mueting, Raasch & Gebhardt P.A.

(57) ABSTRACT

The blood treatment apparatus described herein include a plurality of treatment solution reservoirs connected to a junction which feeds an output controller through an output line. The reservoirs feed the junction through one or more liquid-gas separation filters that limit or prevent air from passing. One or more of the reservoirs can typically be emptied during a treatment session without drawing air into the system.

22 Claims, 5 Drawing Sheets

(56) References Cited

U.S. PATENT DOCUMENTS

| | | | | |
|---|---|---|---|---|
| 4,925,444 | A * | 5/1990 | Orkin | A61M 5/16827 123/DIG. 13 |
| 5,114,580 | A * | 5/1992 | Ahmad | A61M 1/3649 210/143 |
| 5,308,333 | A | 5/1994 | Skakoon | |
| 5,451,321 | A | 9/1995 | Matkovich | |
| 5,863,436 | A | 1/1999 | Matkovich | |
| 6,086,770 | A | 1/2000 | Matkovich | |
| 6,111,119 | A * | 8/2000 | Trout | B01D 11/0219 554/12 |
| 7,588,722 | B2 | 9/2009 | Chevallet | |
| 7,618,542 | B2 | 11/2009 | Okazaki | |
| 2001/0037078 | A1 | 11/2001 | Lynn | |
| 2003/0009123 | A1* | 1/2003 | Brugger | A61M 1/3626 604/4.01 |
| 2004/0043224 | A1 | 3/2004 | Sternberg | |
| 2005/0171501 | A1 | 8/2005 | Kelly | |
| 2006/0213187 | A1* | 9/2006 | Kupe | B01D 53/9431 60/286 |
| 2007/0055198 | A1* | 3/2007 | O'Mahony et al. | 604/67 |
| 2007/0135765 | A1* | 6/2007 | Miller et al. | 604/131 |
| 2009/0008306 | A1* | 1/2009 | Cicchello et al. | 210/85 |
| 2009/0107335 | A1* | 4/2009 | Wilt | B01D 19/00 95/261 |
| 2009/0107902 | A1* | 4/2009 | Childers | A61M 1/16 210/196 |
| 2010/0204765 | A1* | 8/2010 | Hall | A61F 7/12 607/105 |
| 2011/0004187 | A1 | 1/2011 | Beiriger | |
| 2011/0281319 | A1* | 11/2011 | Swayze | B01D 21/283 435/173.9 |
| 2012/0031826 | A1* | 2/2012 | Childers | A61M 1/16 210/195.2 |
| 2012/0043279 | A1 | 2/2012 | Kelly | |

FOREIGN PATENT DOCUMENTS

| | | |
|---|---|---|
| EP | 0 081 655 B1 | 9/1985 |
| EP | 0 247 213 A1 | 12/1987 |
| EP | 1 543 853 B1 | 6/2005 |
| GB | 2 043 478 A | 10/1980 |
| GB | 2 250 342 A | 6/1992 |
| WO | 81/01248 | 5/1981 |
| WO | 90/11812 | 10/1990 |
| WO | 91/17809 | 11/1991 |

* cited by examiner

EXTRACORPOREAL BLOOD TREATMENT APPARATUS WITH MULTIPLE TREATMENT SOLUTION RESERVOIRS

Extracorporeal blood treatment apparatus having multiple treatment solution reservoirs and associated methods are described herein.

BACKGROUND

Extracorporeal blood treatment means taking the blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment is used with patients incapable of effectively eliminating matter from their blood, for example in the case of a patient who is suffering from temporary or permanent kidney failure. These and other patients may undergo extracorporeal blood treatment to add to or to eliminate matter from their blood, to maintain an acid-base balance or to eliminate excess body fluids, for instance.

Extracorporeal blood treatment is typically performed by sampling the patient's blood in a continuous flow, by introducing the blood into a primary chamber of a filter that is defined, at least in part, by a semi-permeable membrane. The semi-permeable membrane may selectively allow the unwanted matter contained in the blood pass through the membrane, from the primary chamber to the secondary chamber, and may selectively allow the beneficial matter contained in the liquid going into the secondary chamber pass through the membrane to the blood going into the primary chamber, according to the type of treatment.

A number of extracorporeal blood treatments may be performed by the same machine. In ultrafiltration (UF) treatment, the unwanted matter is eliminated from the blood by convection through the membrane in the secondary chamber.

In hemofiltration (HF) treatment, the blood runs through a chamber that is defined, at least in part, by a semi-permeable membrane as in UF, and the beneficial matter is added to the blood, typically by the introduction of a fluid into the blood, either before, or after its passage through the filter and before it is returned to the patient.

In hemodialysis (HD) treatment, a secondary fluid containing the beneficial matter is introduced into the filter's secondary chamber. The blood's unwanted matter crosses the semi-permeable membrane by diffusion and penetrates into the secondary fluid, and the beneficial matter of the secondary fluid can cross the membrane and penetrate into the blood.

In hemodiafiltration (HDF) treatment, the blood and the secondary fluid exchange their matter as in HD, and further, matter is added to the blood, typically by introducing a fluid into the treated blood before it is returned to the patient as in HF; unwanted matters are eliminated from the blood by convection and diffusion.

In those treatments using a secondary fluid, the secondary fluid goes through the filter's secondary chamber and receives the blood's unwanted matter by diffusion and/or convection through the membrane. This liquid is then extracted from the filter: it is commonly called effluent, and is sent to a drain or to a receptacle then intended to be discharged into a drain.

In the extracorporeal treatments that use a secondary fluid, the secondary fluid may be supplied in a sterile single-use bag as illustrated in FIG. 1. For purposes of this discussion, the secondary fluid may be dialysate contained in a dialysate bag 11. The dialysate bag 11 delivers dialysate to the secondary chamber 4 through an exit line 9. This bag 11 is combined with a gravimetric scale 21 linked to a control unit 41. Thus, weight signals are transmitted to the control unit 41 that is capable of monitoring the weight changes of the bag 11 and to control a pump 31 acting on the exit line 9 (i.e., the line delivering dialysate from the bag 11 to the secondary chamber 4).

Regardless of whether the control of dialysate delivery is accomplished gravimetrically or volumetrically, a single-use dialysate bag 11 is often emptied well before the end of the session. This phenomenon is all the more pronounced during an intensive treatment. Indeed, one wishes both to exchange a large quantity of liquid in HF or HDF therapy, and to perform long-term treatments.

As soon as the bag 11 reaches a set level (or at another time as selected by a user), the pump acting on the exit line 9 (and other pumps as needed) may be temporarily stopped, while the blood may continue to circulate extracorporeally in the filter's primary chamber 3. Once the pump 31 is stopped, the user has to disconnect and unhook the empty dialysate bag 11. Then the user attaches and connects a new full single-use bag 11 to the treatment apparatus and restarts the pump(s) to return to the extracorporeal treatment with fluid circulation through the two chambers (3, 4) of the filter 2.

This bag replacement operation has several potential disadvantages. The operation is performed by health care personnel who have to monitor several patients at the same time (a waiting time before action by the personnel typically increases therapy down time and may require additional treatment time or result in decreased treatment efficiency), and the regular changing of the dialysate bag during a session adds an economic cost to the treatment.

Although described herein in connection with the delivery of dialysate, it should be understood that similar issues may be encountered in blood treatment apparatus in which infusion fluids are delivered into the blood (whether before or after filter or before the blood pump). For purposes of the discussions herein, any such fluids will be referred to as "treatment solutions" which may include, e.g., dialysate; a replacement fluid of a convective replacement therapy of the renal function; plasma, albumin or colloid solutions that may be used in Therapeutic Plasma Exchange (TPE); or any other known type of medical fluid for replacement therapy.

SUMMARY

The blood treatment apparatus described herein include a plurality of treatment solution reservoirs connected in parallel with a junction which feeds an output controller through an output line. The reservoirs feed the output controller junction through a tubing set that includes one or more liquid-gas separation filters that limit or prevent air from passing downstream so that it reaches the output flow controller. As a result, one or more of the treatment solution reservoirs can typically be emptied during a treatment session without passing air into the blood treatment apparatus downstream of the output flow controller.

When treatment solution reservoirs are connected in parallel with the junction, emptying of the treatment solution reservoirs through the junction could or should theoretically occur at the same rate. In reality, however, the treatment solution reservoirs will often empty at different rates. Differences in the rate of emptying may be caused by, e.g., differences in the amount of treatment solution in the reservoirs, the height of the reservoirs relative to each other, differences in the quality of the connection between the treatment solution reservoir and the fluid lines used to remove treatment solution from the reservoir, kinks or other fluid flow limiters in the lines, etc.

Those differences in the rate of emptying could be problematic if, for example, air could be drawn into the treatment solution delivery system from an empty reservoir. As described herein, however, one or more liquid-gas separation filters limit or prevent the entry of air into the system from an empty reservoir while one or more treatment solution reservoirs that still contain treatment solution and are connected in parallel with the empty treatment solution reservoir continue to deliver treatment solution to the output controller.

The blood treatment apparatus described herein may also include a reservoir status monitor configured to determine when a treatment solution reservoir requires replacement. While a treatment solution reservoir requires replacement if it is empty, in some embodiments of the apparatus and methods described herein, it may be determined that one or more treatment solution reservoirs require replacement when the one or more reservoirs still contain some treatment solution. In other words, a determination that a treatment solution reservoir requires replacement does not require that the reservoir actually be empty.

One potential benefit of some embodiments of the blood treatment apparatus described herein is that the combination of multiple treatment solution reservoirs connected in parallel and one or more liquid-gas separation filters can provide the ability to completely empty at least one of the reservoirs during a treatment session while substantially preventing the entry of air from an empty reservoir into the blood treatment apparatus.

Another potential advantage of some embodiments of the blood treatment apparatus described herein is that uninterrupted treatment duration can potentially be increased because additional treatment solution (in the form of two or more parallel connected reservoirs) can be provided in the system and, potentially, the delivery of treatment solution from the reservoir or reservoirs that contain treatment solution can continue while an empty reservoir is replaced or refilled.

In blood treatment apparatus that rely on weight of the reservoirs to make a determination that a reservoir is empty, a potential benefit is that one scale can be used to weigh two or more of the parallel-connected reservoirs at the same time. The use of one scale to weigh multiple reservoirs can potentially reduce the cost and complexity of the blood treatment apparatus.

Another potential advantage of some embodiments of the blood treatment apparatus described herein may be found in the limiting of air intake into the blood circuit. Limiting air intake as described herein can reduce foam generation in the hemodialyzer outlet and/or in an air trap used to remove air entrained in blood within the blood circuit, which can lead to improved level control within the apparatus.

In one aspect, some embodiments of an extracorporeal blood treatment apparatus as described herein may include: a blood circuit that includes an arterial line intended to draw blood from a patient and a venous line intended to return blood to the patient; and a treatment solution delivery system configured to deliver treatment solution within the blood treatment apparatus through a treatment solution port. The treatment solution delivery system may include a plurality of treatment solution reservoirs, wherein each treatment solution reservoir of the plurality of treatment solution reservoirs comprises an outlet; a tubing set comprising a junction, a plurality of feeder lines connected to the junction, and an outlet line connected to the junction, the tubing set configured to deliver treatment solution from the plurality of treatment solution reservoirs to the outlet line through the junction; a reservoir status monitor configured to determine when a treatment solution reservoir of the plurality of treatment solution reservoirs requires replacement; at least one liquid-gas separation filter positioned in the tubing set, wherein all treatment solution passing through the outlet line passes through the at least one liquid-gas separation filter; an output flow controller operatively connected to the outlet line, wherein the output flow controller is configured to deliver treatment solution from the plurality of treatment solution reservoirs to the treatment solution port; and a control unit operably connected to the output flow controller, wherein the control unit is configured to operate the output flow controller.

In some embodiments of the blood treatment apparatus described herein, the volume of treatment solution in the tubing set between the plurality of treatment solution reservoirs and the at least one liquid-gas separation filter is less than the volume of treatment solution between the at least one liquid-gas separation filter and the output flow controller.

In some embodiments of the blood treatment apparatus described herein, the at least one liquid-gas separation filter in the tubing set comprises a separate liquid-gas separation filter in each feeder line of the plurality of feeder lines.

In some embodiments of the blood treatment apparatus described herein, the at least one liquid-gas separation filter in the tubing set comprises only one liquid-gas separation filter located downstream of the feeder lines.

In some embodiments of the blood treatment apparatus described herein, the liquid-gas separation filter is located at the junction in the tubing set.

In some embodiments of the blood treatment apparatus described herein, the at least one liquid-gas separation filter comprises a sterilizing filter.

In some embodiments of the blood treatment apparatus described herein, the reservoir status monitor comprises at least one pressure sensor configured to measure treatment solution fluid pressure in the tubing set, and wherein the at least one pressure sensor is operably connected to the control unit. In some embodiments, the at least one pressure sensor comprises a pressure sensor configured to measure treatment solution fluid pressure downstream from the feeder lines and upstream from the output controller. In some embodiments, the at least one pressure sensor comprises a separate pressure sensor in each feeder line of the plurality of feeder lines, wherein each pressure sensor is configured to measure the treatment solution fluid pressure in one feeder line of the plurality of feeder lines.

In some embodiments of the blood treatment apparatus described herein, the reservoir status monitor comprises a sensor configured to detect treatment solution in the tubing set downstream from the empty treatment solution reservoir and upstream of the junction.

In some embodiments of the blood treatment apparatus described herein, the reservoir status monitor comprises a gravimetric scale configured to measure the combined weight of the plurality of treatment solution reservoirs at the same time.

In some embodiments of the blood treatment apparatus described herein, the control unit is configured to operate the output flow controller in reverse under selected conditions such that a portion of treatment solution from the tubing set is delivered back into at least one treatment solution reservoir of the plurality of treatment solution reservoirs.

In another aspect, methods of controlling treatment solution flow in the extracorporeal blood treatment apparatus described herein are provided. The blood treatment apparatus may include a blood circuit and a treatment solution delivery system configured to deliver treatment solution within the blood treatment apparatus through a treatment solution port, wherein the treatment solution delivery system includes a plurality of treatment solution reservoirs and a tubing set that includes a junction, a plurality of feeder lines connected to the junction, and an outlet line connected to the junction, the tubing set configured to deliver treatment solution from the plurality of treatment solution reservoirs to the outlet line through the junction. The methods of delivering treatment solution using the blood treatment apparatus described herein may include: delivering treatment solution from the plurality of treatment solution reservoirs to an output flow controller through the tubing set, wherein the treatment solution passes through a liquid-gas separation filter between the plurality of treatment solution reservoirs and the output flow controller; determining when at least one treatment solution reservoir of the plurality of treatment solution reservoirs requires replacement; and controlling operation of the output flow controller based at least in part on the determination that at least one treatment solution reservoir of the plurality of treatment solution reservoirs requires replacement.

In some embodiments of the methods of controlling treatment solution flow as described herein, the volume of treatment solution in the tubing set between the plurality of treatment solution reservoirs and the liquid-gas separation filter is less than the volume of treatment solution between the liquid-gas separation filter and the output flow controller, and the method further comprises operating the output flow controller in reverse after replacing at least one treatment solution reservoir of the plurality of treatment solution reservoirs such that a portion of treatment solution in the tubing set between the liquid-gas separation filter and the output flow controller is delivered back into the tubing set between the liquid-gas separation filter and the plurality of treatment solution reservoirs.

In some embodiments of the methods of controlling treatment solution flow as described herein, the tubing set comprises a liquid-gas separation filter located in each feeder line of the plurality of feeder lines, and wherein treatment solution delivered to the outlet line from each feeder line passes through the liquid-gas separation filter in each feeder line.

In some embodiments of the methods of controlling treatment solution flow as described herein, the tubing set comprises only one liquid-gas separation filter that is located downstream of the feeder lines such that all of the treatment solution delivered to the output flow controller passes through the liquid-gas separation filter.

In some embodiments of the methods of controlling treatment solution flow as described herein, the liquid-gas separation filter is located at the junction in the tubing set.

In some embodiments of the methods of controlling treatment solution flow as described herein, determining when at least one treatment solution reservoir of the plurality of treatment solution reservoirs requires replacement comprises weighing the plurality of treatment solution reservoirs at the same time using a single gravimetric scale.

In some embodiments of the methods of controlling treatment solution flow as described herein, determining when at least one treatment solution reservoir of the plurality of treatment solution reservoirs requires replacement comprises measuring treatment solution fluid pressure in the tubing set. In some embodiments the pressure may be measured upstream of the junction. In some embodiments, the pressure may be measured downstream from the feeder lines and upstream of the output controller.

In some embodiments of the methods of controlling treatment solution flow as described herein, determining when at least one treatment solution reservoir of the plurality of treatment solution reservoirs requires replacement comprises sensing treatment solution in the tubing set upstream of the junction.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

The above summary is not intended to describe each embodiment or every implementation of the blood treatment apparatus described herein. Rather, a more complete understanding of the invention will become apparent and appreciated by reference to the following Description of Illustrative Embodiments and claims in view of the accompanying figures of the drawing.

DESCRIPTION OF ILLUSTRATIVE EMBODIMENTS

Figure 1:
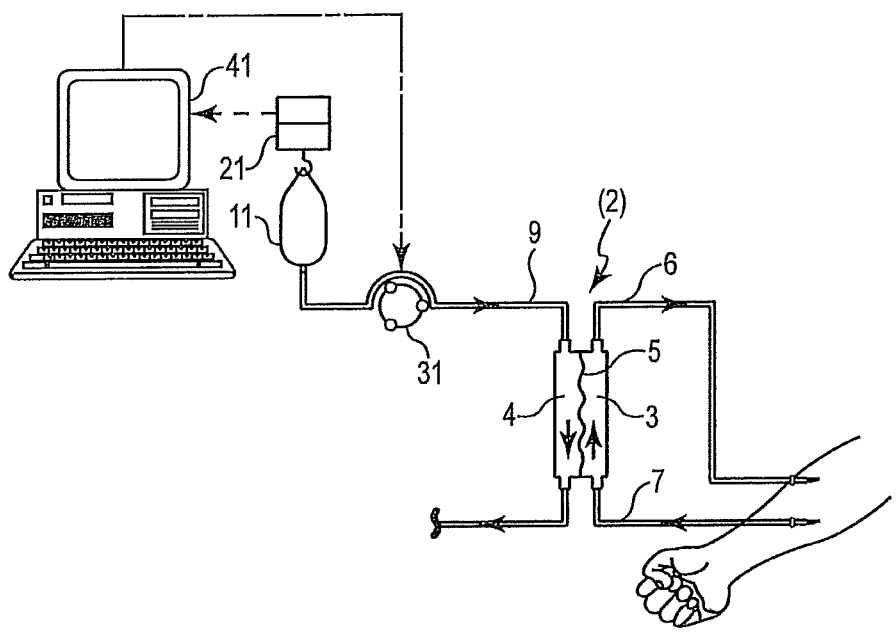
FIG. 1 depicts a known extracorporeal blood treatment apparatus.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

In the various illustrative embodiments of FIGS. 2-5, a blood treatment apparatus 1 is depicted. The depicted blood treatment apparatus 1 is in an operational configuration that enables it to perform a hemodialysis treatment. The other treatment configurations mentioned previously (ultrafiltration, hemofiltration, and hemodiafiltration), as well as others, are of course possible within other embodiments, and the principles, apparatus, and methods described herein may be applied in those embodiments as well.

The extracorporeal blood treatment apparatus described herein may include a control unit used to control the various components in the apparatus (e.g., control units 41 in the embodiments depicted in FIGS. 2-5). The control unit may be provided in any suitable form and may, for example, include memory and a controller. The controller may, for example, be in the form of one or more microprocessors, Application Specific Integrated Circuit (ASIC) state machines, etc. The control units may include a variety of any suitable input devices configured to allow a user to operate the apparatus (e.g., keyboards, touchscreens, mice, trackballs, etc.), as well as display devices configured to convey information to a user (e.g., monitors (which may or may not be touchscreens), indicator lights, etc.).

In the various illustrative embodiments of the blood treatment apparatus described herein, a plurality of treatment solution reservoirs are connected in parallel with an output controller such that the plurality of treatment solution reservoirs are all in fluid communication with a junction which feeds the output controller through an output line. Because all of the reservoirs are in fluid communication with the junction (and, therefore, the output controller), emptying of the reservoirs would theoretically occur at the same rate. In reality, however, the reservoirs will often empty at different rates.

Those differences in the rate of emptying could be problematic if, for example, air is drawn into the treatment solution delivery system from a reservoir that empties first. As described herein, however, liquid-gas separation filters can limit or prevent the entry of air into the system from an empty reservoir while one or more reservoirs that still contain treatment solution and are connected in parallel with the empty reservoir continues to deliver treatment solution to the output controller. The blood treatment apparatus described herein may also include a reservoir status monitor configured to determine when a treatment solution reservoir is empty.

The blood treatment apparatus 1 depicted in FIGS. 2-5 (which, as described herein, is in an operational configuration that enables it to perform a hemodialysis treatment) includes a filter 2 having a primary chamber 3 and a secondary chamber 4 separated by a semi-permeable membrane 5. A blood circuit in the blood treatment apparatus 1 includes an arterial line 7 intended to draw blood from the patient, the filter's primary chamber 3 and a venous line 6 intended to return blood to the patient from the primary chamber 3.

Treatment solution (e.g., dialysate, etc.) is delivered to the blood treatment apparatus 1 in the blood treatment apparatus described herein. Because the treatment solution in each of the embodiments depicted in FIGS. 2-5 is dialysate, the treatment solution is delivered to the secondary chamber 4 of the filter 2 through a treatment solution port 10 connected to inlet line 9 using output controller 31. Liquids (e.g., effluent) are removed from the secondary chamber 4 of the filter 2 through an effluent line 8.

Although each embodiment of the blood treatment apparatus depicted in FIGS. 2-5 involves delivery of treatment solution (in the form of, e.g., dialysate) to the secondary chamber 4 of the filter 2 through treatment solution port 10 connected to inlet line 9, other treatment solutions may, in other embodiments, be delivered directly to blood in the arterial line 7 and/or venous line 6 (or even, in some embodiments, into the blood resident in primary chamber 3).

In the embodiments of the blood treatment apparatus 1 depicted in FIGS. 2-5, the treatment solution is supplied to the treatment solution port 10 from the first reservoir 11 and second reservoir 12 using an output controller 31. As used herein, the term "reservoir" can include any suitable structure in which liquids can be stored, e.g., bags, bottles, containers, etc.

Further, although the output controller 31 is, in the embodiments of FIGS. 2-5 depicted in the form of a peristaltic pump, the output controller 31 may be provided in a variety of alternative forms that can be used to control the flow of the treatment solution to the port 10 including, e.g., other pumps (e.g., piston pumps, diaphragm pumps, etc.), other flow control mechanisms (e.g., valves, clamps, etc.), etc.

In the embodiments depicted in FIGS. 2-5, the same treatment solution is contained in the reservoirs. In still other embodiments, the blood treatment apparatus as described herein may include the delivery of two or more different treatment solutions to the same or different locations within the blood treatment apparatus. For example, treatment solution in the form of dialysate may be delivered to the secondary chamber 4 of the filter as depicted in the embodiments of FIGS. 2-5 while one or more different treatment solutions are delivered to, e.g., the blood in primary chamber 3, arterial line 7, and/or venous line 6. Each different treatment solution delivered within the blood treatment apparatus could potentially be delivered using a separate set of parallel reservoirs connected to a separate output controller.

Although the embodiments depicted in FIGS. 2-5 include two reservoirs 11 and 12, other embodiments may be operated with three or more reservoirs containing treatment solution connected in parallel with a junction. Also, in some embodiments, the reservoirs may all contain the same volume of treatment solution, while in other embodiments the reservoirs may contain different volumes of treatment solution.

The treatment solution reservoirs of the blood treatment apparatus described herein are fluidly connected to the output controller 31 and the output port 10 by a tubing set. The tubing sets of the embodiments depicted in FIGS. 2-5 include a first feeder line 61 that is configured to connect to the first reservoir 11, a second feeder line 62 that is configured to connect to the second reservoir 12, a junction 63 to which the feeder lines 61 and 62 are connected, and an outlet line 64 connected to the junction 63. When the first and second feeder lines 61 and 62 are connected to the first and second reservoirs 11 and 12 as depicted, treatment solution in the reservoirs 11 and/or 12 flows into the junction 63 through the feeder lines 61 and 62 and flows out of the junction 63 through the outlet line 64.

In the embodiments of the blood treatment apparatus depicted in FIGS. 2-5, the feeder line 61 includes a liquid-gas separation filter 71 and the feeder line 62 includes a liquid-gas separation filter 72. The liquid-gas separation filters 71 and 72 preferentially pass liquids while substantially preventing the passage of gas (e.g., air). The filters 71 and 72 may include, e.g., a vent or other mechanism for expelling any gas that is separated from the fluid passing into the filter. Because each of the feeder lines includes a liquid-gas separation filter, all of the treatment solution delivered to the outlet line 64 of the tubing set passes through at least one liquid-gas separation filter 71 or 72.

The liquid-gas separation filters 71 and 72 may, in some embodiments, include hydrophilic media through which the liquid passes and a hydrophobic membrane to provide a vent for gas separated from the liquid that is allowed to pass through the filter. In some embodiments, the liquid-gas separation filters used in the tubing sets described herein may be sterilizing filters, i.e., filters that are designed to remove unwanted microorganisms and other materials from a liquid that are considered unsterile. One potentially useful sterilizing filter may provide its sterilizing capabilities based on size exclusion, e.g., a 0.45 µm (micron), a 0.22 µm (micron) filter, etc., may provide the sterilizing function by removing unwanted organisms from the fluid passing through the filter.

The liquid-gas separation filters 71 and 72 may be integrated into their respective feeder line 61 or 62 at an intermediate location along the feeder line between the reservoir and the junction 63. In some embodiments, the filters 71 and 72 in each of the feeder lines 61 and 62 are located closer to the treatment solution reservoir 11 or 12 than the junction 63. In some embodiments, the feeder lines may be described as having distal ends connected to the reservoirs and the liquid-gas separation filters may be located proximate the distal ends of the feeder lines.

One potential advantage of placing the liquid-gas separation filters closer to the reservoirs is that the volume of air in a feeder line that leads to an empty reservoir would be reduced as compared to a system in which the liquid-gas separation filter is located farther away from the empty reservoir. In some embodiments, the volume of treatment solution in the tubing set between the plurality of treatment solution reservoirs and any liquid-gas separation filters is less than the volume of treatment solution between the liquid-gas separation filters and the output flow controller. In the embodiment depicted in FIG. 2, that volumetric relationship can be controlled, at least in part, by selecting locations for the liquid-gas separation filters that are closer to the reservoirs 11 and 12.

Because the liquid-gas separation filters used in the feeder lines preferentially pass liquid while substantially preventing the passage of gases, the reservoirs to which the feeder lines are attached can be emptied of treatment solution as described herein while the risk of drawing air into the system from an empty reservoir is reduced or eliminated. In operation, fluid flow through the liquid-gas separation filters typically stops when air reaches the filter after it has been wetted by the liquid treatment solution during use. As discussed herein, locating the filters closer to the reservoirs can limit the amount of air drawn into the feeder lines from empty reservoirs and/or air that could be allowed into the feeder line when, e.g., disconnecting a reservoir (e.g., an empty reservoir) to replace it with a different (e.g., full) reservoir.

The feeder lines 61 and 62 may be connected to the reservoirs 11 and 12 using, e.g., Luer connectors, spikes, or any other suitable fluid connection. The specific construction of the connectors can vary so long as an appropriate (e.g., a liquid-tight) connection can be made. In some embodiments, the liquid-gas separation filters maybe incorporated into the connectors used to connect the feeder lines to the reservoirs, although such a construction is not required.

Although the liquid-gas separation filters 71 and 72 are depicted in the same location along each of their feeder lines 61 and 62, in other embodiments the liquid-gas separation filters may be located in different locations in their respective fluid paths.

Some or all of the different components of the tubing sets (in this or any other embodiments described herein), i.e., the feeder lines 61 and 62, the junction 63, the outlet line 64, liquid-gas separation filters 71 and 72, etc. may be pre-assembled in some embodiments, while in other embodiments some or all of the components may need to be assembled when setting up the blood treatment apparatus 1 for a treatment session.

Figure 2:
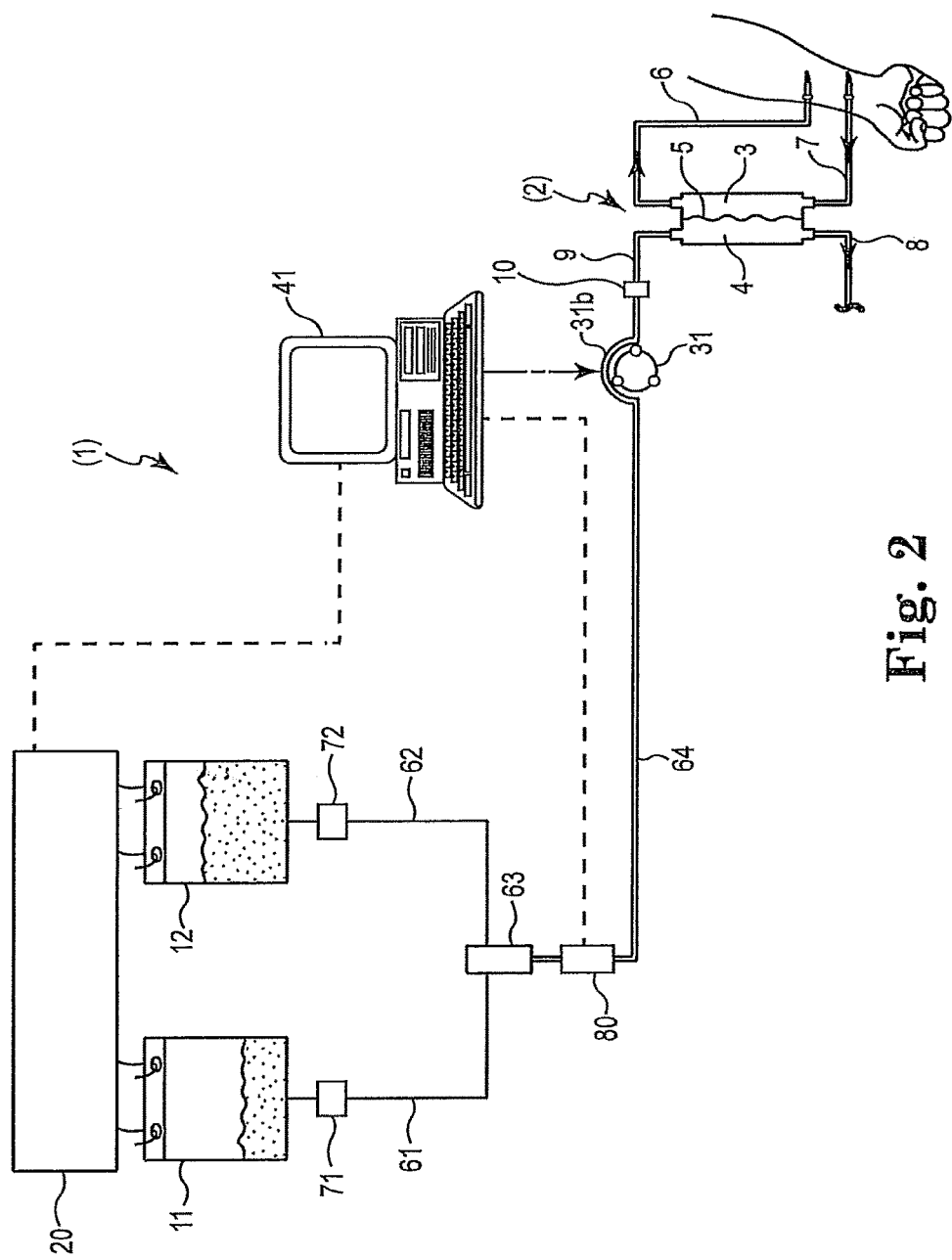
FIG. 2 depicts one embodiment of an extracorporeal blood treatment apparatus as described herein.

Referring now to the embodiment of the blood treatment apparatus 1 depicted in FIG. 2, a gravimetric scale 20 may be provided and be configured to weigh both the first reservoir 11 and the second reservoir 12 at the same time. The weight of the reservoirs is indicative of the amount of treatment solution contained in the first reservoir 11 and the second reservoir 12. The gravimetric scale 20 may, in some embodiments, be a part of the reservoir status monitor used to determine when a treatment solution reservoir may require replacement.

The illustrative embodiment of the blood treatment apparatus 1 depicted in FIG. 2 also includes an optional pressure sensor 80 that may be used to measure fluid pressure downstream from the feeder lines (e.g., lines 61 and 62) and upstream of the output controller 31. The fluid pressure measured by the sensor 80 may be used, in some embodiments, to control the output controller 31 and/or to assist in determining when a reservoir upstream from the pressure sensor 80 has been emptied or otherwise requires replacement. In such an embodiment, the optional pressure sensor 80 may be considered as a component of the reservoir status monitor along with the gravimetric scale 20 while in other embodiments the pressure sensor 80 may be the only sensor used in the reservoir status monitor.

Another feature depicted in the illustrative embodiment of the blood treatment apparatus depicted in FIG. 2 is a control unit 41 is linked to the gravimetric scale 20, the output controller 31, and the optional pressure sensor 80. The control unit 41 may be configured to control the output controller 31 to provide flow of the treatment solution to the treatment solution port 10 during the treatment delivered using the blood treatment apparatus (at a constant flow rate and/or at a variable flow rate according to a selected flow rate profile).

In the embodiment depicted in FIG. 2, the weight information supplied to the control unit 41 by the gravimetric scale system 20 can be used to monitor the amount of treatment solution in the reservoirs so that the reservoirs can be refilled or replaced when needed. Because the individual weight of the reservoirs is not measured, operation of the blood treatment apparatus 1 may be interrupted to replace all of the reservoirs when the combined weight of the reservoirs reaches a selected level that would lead to a determination that one or more of the reservoirs may be empty or otherwise require replacement.

In some embodiments of the blood treatment apparatus described herein that include gravimetric scales that are configured to weigh the treatment solution reservoirs, the weight information from the gravimetric scale 20 can potentially be used to monitor the amount of treatment solution flowing out of the reservoirs and into the output flow controller 31 and/or the flow rate of the treatment solution.

Figure 3:
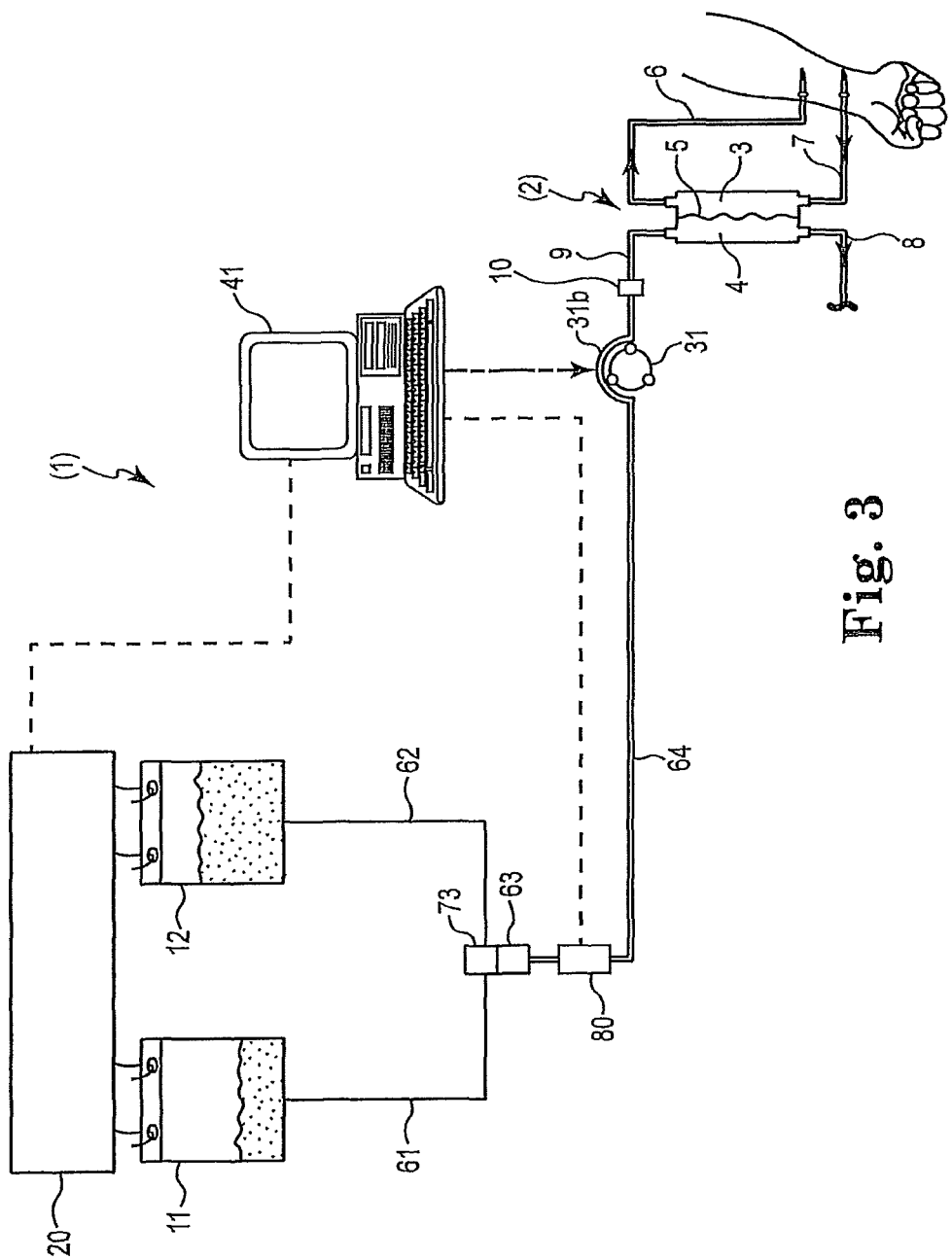
FIG. 3 depicts another embodiment of an extracorporeal blood treatment apparatus as described herein.

Another illustrative embodiment of a blood treatment apparatus 1 is depicted in FIG. 3. Like the embodiment of the blood treatment apparatus depicted in FIG. 2, the blood treatment apparatus 1 depicted in FIG. 3 also includes a gravimetric scale 20 configured to weigh both the first reservoir 11 and the second reservoir 12 at the same time. The weight of the reservoirs is indicative of the amount of treatment solution contained in the first reservoir 11 and the second reservoir 12. The gravimetric scale 20 may, in some embodiments, be a part of the reservoir status monitor used to determine when a treatment solution reservoir requires replacement. The blood treatment apparatus 1 depicted in FIG. 3 includes feeder lines 61 and 62 connected to the reservoirs 11 and 12 as discussed above in connection with the embodiment depicted in FIG. 2.

Unlike the embodiment of blood treatment apparatus in which each of the feeder lines includes a separate liquid-gas separation filter, the embodiment of blood treatment apparatus depicted in FIG. 3 includes a liquid-gas separation filter 73 that is positioned in the tubing set such that all of the treatment solution passing through the outlet line 64 passes through the liquid-gas separation filter 73 such that air entering the tubing set upstream of the liquid-gas separation filter 73 (e.g., from an empty treatment solution reservoir) does not reach the output flow controller 31. This control over the passage of air can, in the embodiment depicted in FIG. 3, be achieved using only one liquid-gas separation filter 73.

Also included in the blood treatment apparatus depicted in FIG. 3 is an optional pressure sensor 80 that may be used to measure fluid pressure downstream from the feeder lines (e.g., lines 61 and 62) and upstream of the output controller 31. The fluid pressure measured by the sensor 80 may be used, in some embodiments, to control the output controller 31 and/or to assist in determining when a reservoir upstream from the pressure sensor 80 has been emptied. In such an embodiment, the optional pressure sensor 80 may be considered as a component of the reservoir status monitor along with the gravimetric scale 20 while in other embodiments the pressure sensor 80 may be the only sensor used in the reservoir status monitor.

Another feature depicted in the illustrative embodiment of the blood treatment apparatus depicted in FIG. 3 is a control unit 41 that is linked to the gravimetric scale 20, the output controller 31, and the optional pressure sensor 80. The control unit 41 may be configured to control the output controller 31 to provide flow of the treatment solution to the treatment solution port 10 during the treatment delivered using the blood treatment apparatus (at a constant flow rate and/or at a variable flow rate according to a selected flow rate profile).

In the embodiment depicted in FIG. 3, the weight information supplied to the control unit 41 by the gravimetric scale system 20 can be used to monitor the amount of treatment solution in the reservoirs so that the reservoirs can be refilled or replaced when needed as discussed above in connection with the embodiment depicted in FIG. 2. Further, the weight information from the gravimetric scale 20 can potentially be used to monitor the amount of treatment solution flowing out of the reservoirs and into the output flow controller 31 and/or the flow rate of the treatment solution.

Figure 4:
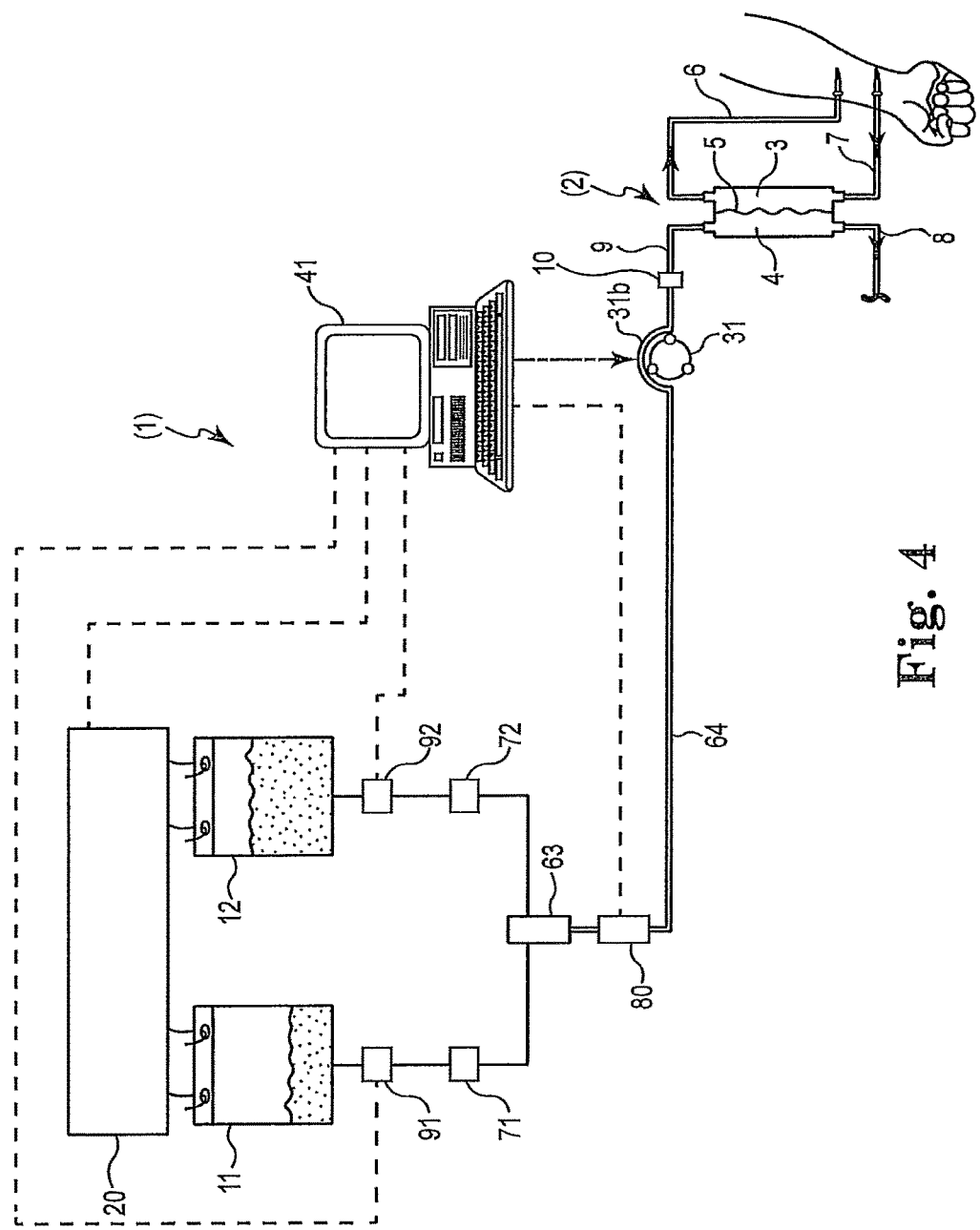
FIG. 4 depicts another embodiment of an extracorporeal blood treatment apparatus as described herein.

Referring to the illustrative embodiment of a blood treatment apparatus as depicted in FIG. 4, the blood treatment apparatus 1 includes components that are common to the embodiment depicted in FIG. 2 such as, e.g., the first reservoir 11, second reservoir 12, gravimetric scale 20, output controller 31, control unit 41, feeder lines 61 and 62, junction 63, output line 64, liquid-gas separation filters 71 and 72, and optional pressure sensor 80.

Among the differences in the embodiment depicted in FIG. 4 as compared to the embodiment depicted in FIG. 2 are the sensors 91 and 92 on the feeder lines 61 and 62. The sensors 91 and 92 may be configured to detect treatment solution in the tubing set. That detection may be performed by affirmatively detecting the presence of treatment solution in the tubing set or, alternatively, the absence of treatment solution in the tubing set (where, e.g., the sensor may detect air rather than the treatment solution). The sensors 91 and 92 may use any suitable technique or combination of techniques to detect the presence or absence of treatment solution in the tubing set. Examples of some potentially suitable sensors may include, but are not limited to optical sensors, capacitive sensors, ultrasonic sensors, etc.

The sensors 91 and 92 may function as components of the reservoir status monitor for the blood treatment apparatus 1 of FIG. 4. In some embodiments, the sensors 91 and 92 may be used in combination with the gravimetric scale 20 to function as the reservoir status monitor for the blood treatment apparatus 1 while in other embodiments the sensors 91 and 92 may be the only sensors used in the reservoir status monitor.

Figure 5:
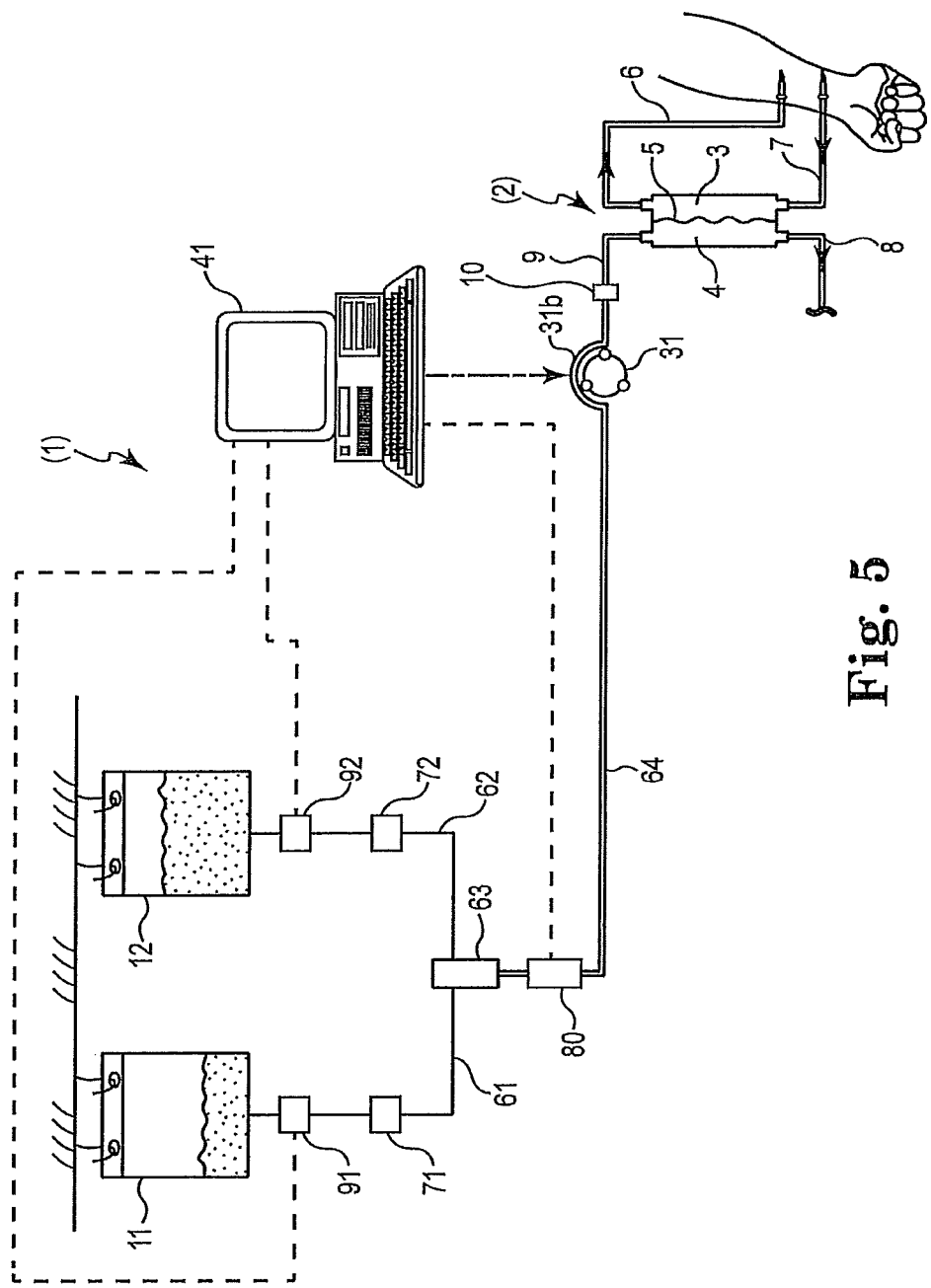
FIG. 5 depicts another embodiment of an extracorporeal blood treatment apparatus as described herein.

Referring to the illustrative embodiment of a blood treatment apparatus as depicted in FIG. 5, the blood treatment apparatus 1 includes components that are common to the embodiments depicted in FIGS. 2 and 3 such as, e.g., the first reservoir 11, second reservoir 12, output controller 31, control unit 41, feeder lines 61 and 62, junction 63, output line 64, liquid-gas separation filters 71 and 72, and optional pressure sensor 80.

The embodiment depicted in FIG. 5 also includes components that are provided in the embodiment depicted in FIG. 4 such as, e.g., sensors 91 and 92 that may, as described in connection with that embodiment, be in the form of pressure sensors, optical sensors, capacitive sensors, ultrasonic sensors, etc. As provided in the embodiment depicted in FIG. 5, the sensors 91 and 92 may be considered optional if the pressure sensor 80 is provided. In other words, the embodiment of the blood treatment apparatus 1 depicted in FIG. 5 may or may not include the sensors 91 and 92. If the sensors 91 and 92 are not included, then the pressure sensor 80 should be included so that a determination can be made as to when a reservoir is empty as described herein.

One difference in the embodiment depicted in FIG. 5 is the lack of a gravimetric scale such as that found in the illustrative embodiments of the blood treatment apparatus depicted in FIGS. 2 and 3. In the absence of a measurement of the reservoir weight, the reservoir status monitor in the depicted embodiment may be constituted by the sensors 91 and 92 and/or the pressure sensor 80. For example, determinations as to whether or not one or more of the reservoirs are empty may be, in the embodiment depicted in FIG. 5, based on fluid pressure measurements (using sensors 91 and 92 and/or sensor 80) and/or detection of treatment solution in the feeder lines (if the sensors 91 and 92 are optical/capacitive/ultrasonic/etc. sensors as discussed herein).

Illustrative methods of controlling treatment solution flow in the blood treatment apparatus described herein may involve the following operations. After arranging the components as described herein, two (or more) reservoirs 11 and 12 may be connected to a gravimetric scale (if the system includes one). As a result, the scale will measure the combined weight of the reservoirs. A feeder line can be connected to each of the reservoirs using, as described herein, any appropriate connection mechanism (e.g., Luer locks, spikes, etc.). Priming of the feeder lines and the connected components may then be initiated so that the liquid-gas separation filters in the feeder lines can be wetted to properly restrict flow of gas through the filters as described herein.

Because the treatment solution reservoirs are connected in parallel to the junction through their feeder lines, treatment solution in both of the reservoirs can flow through the junction and to the output controller as discussed above. In a perfectly balanced system, treatment solution would be removed from each reservoir at the same rate. Such perfect balance, however, is not guaranteed and treatment solution will often be removed from one of the reservoirs at a faster rate. In some instances, the flow rate may be affected by, e.g., kinks in the feeder lines, different quality connections to the reservoirs (e.g., a partially broken pin in a pin connector, etc.).

The reservoir from which treatment fluid is removed faster will eventually reach an empty state first and, as a result, air from the reservoir will typically advance to the liquid-gas separation filter, where its further advance towards the junction is halted by the filter. Once treatment solution stops flowing into the junction from the empty reservoir, treatment solution from other reservoirs that are connected to the junction can still flow into the junction. In other words, the flow will essentially automatically switch to the reservoirs that still contain treatment solution.

The blood treatment apparatus described herein include a reservoir fill status monitor that may take a variety of different forms. For example, the reservoir status monitor may be in the form of a gravimetric scale, one or more pressure sensors, one or more optical/capacitive sensors, combinations of a scale and one or more pressure and/or optical/capacitive sensors, etc. Regardless of its form, the reservoir status monitor functions to determine when a treatment solution reservoir in the blood treatment status is empty. When a determination is made that a reservoir is empty, the output controller to which the treatment solution is flowing may be stopped (although in some embodiments in which one or more other reservoirs still contain treatment solution, the output controller may continue to deliver treatment solution from those reservoirs). An alarm, alert, etc. can also be activated to initiate a change in the reservoirs, refilling of the reservoirs, etc. If the reservoirs are to be replaced, the feeder lines may be closed using, e.g., clamps, valves, etc. to limit entry of air into the feeder lines and/or liquid-gas separation filters.

It should be understood that the blood treatment apparatus may, in some embodiments, make a determination that a reservoir is "empty" even when no reservoirs are actually empty. That determination may be made based on, e.g., weight thresholds, pressure thresholds, etc. that indicate that one or more of the reservoirs is likely to be empty or nearly empty.

In blood treatment apparatus that include a gravimetric scale (e.g., the embodiments depicted in FIGS. 2 and 3) that is configured to weigh the reservoirs, the determination that a reservoir is empty may be made when the combined weight of the reservoirs falls to a preselected threshold. In those embodiments that include pressure sensors as described herein, the determination that a reservoir is empty may be made when the pressure in the monitored fluid line or lines falls to a preselected threshold. In those embodiments that include optical/capacitive sensors as described herein, the determination that a reservoir is empty may be made when the optical/capacitive sensors does not detect treatment solution (or detects air) in the monitored fluid line or lines.

In still other embodiments that include a variety of different components to constitute the reservoir status monitor (e.g., a gravimetric scale in combination with one or more pressure sensors and/or one or more optical/capacitive sensors, one or more pressure sensors in combination with one or more optical/capacitive sensors, etc.), the determination that a reservoir is empty can be made on a combination of data received from the different components (e.g., weight in combination with pressure and/or optical/capacitive detection, pressure in combination with optical/capacitive detection, etc.).

After refilling and/or replacement of at least the empty reservoir, the output controller may, in some embodiments, be operated in reverse to force any air out of the feeder lines and/or liquid-gas separation filters with the treatment solution that is contained within the feeder lines. After the period of reverse operation, the output controller may be operated in its normal mode so that treatment solution flows from the reservoirs to the port 10 as described herein. In some embodiments, any air that was located in the feeder lines and/or liquid-gas separation filter may be forced back into a reservoir. In other embodiments in which a liquid-gas separation filter includes a gas vent, air in the filter and/or feeder lines may potentially be forced out of the system through that vent.

The complete disclosure of the patents, patent documents, and publications identified herein are incorporated by reference in their entirety as if each were individually incorporated.

Illustrative embodiments of the blood treatment apparatus and methods of using the same are discussed and reference has been made to possible variations. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An extracorporeal blood treatment apparatus comprising:
   a filter comprising a primary chamber and a secondary chamber separated from the primary chamber by a semi-permeable membrane;
   a blood circuit that includes an arterial line configured to deliver blood from a patient to the primary chamber and a venous line configured to remove the blood from the primary chamber and return the blood to the patient; and
   a treatment solution delivery system configured to deliver treatment solution within the blood treatment apparatus through a treatment solution port, wherein the treatment solution delivery system comprises:
      a plurality of treatment solution reservoirs, wherein each treatment solution reservoir of the plurality of treatment solution reservoirs comprises an outlet, wherein each treatment solution reservoir of the plurality of treatment solution reservoirs contains the same treatment solution;
      a tubing set comprising a junction, a plurality of feeder lines connected to the junction, and an outlet line connected to the junction, wherein each feeder line is attached to one treatment solution reservoir of the plurality of treatment solution reservoirs, the tubing set configured to deliver treatment solution from the plurality of treatment solution reservoirs to the outlet line through the junction;
      a reservoir status monitor configured to determine when a treatment solution reservoir of the plurality of treatment solution reservoirs requires replacement, wherein the reservoir status monitor comprises a gravimetric scale configured to measure the combined weight of the plurality of treatment solution reservoirs at the same time;
      a plurality of a liquid-gas separation filters, wherein liquid-gas separation filter of the plurality of liquid-gas separation filters is positioned in each feeder line of the plurality of feeder lines of the tubing set, wherein each liquid-gas separation filter along each feeder line is located between the junction in the tubing set and the treatment solution reservoir to which the feeder line is attached, wherein all treatment solution passing through the outlet line passes through at least one liquid-gas separation filter, wherein each of the plurality of liquid-gas separation filters comprises a hydrophilic membrane through which the treatment solution passes;

an output flow controller operatively connected to the outlet line and having a first operating mode and a second operating mode, wherein the output flow controller delivers treatment solution from the plurality of treatment solution reservoirs to the treatment solution port in the first operating mode, wherein the plurality of treatment solution reservoirs are in simultaneous fluid communication with the junction of the tubing set through the plurality of feeder lines such that the plurality of treatment solution reservoirs empty simultaneously as the treatment solution flows through the outlet line to the output flow controller; and a control unit operably connected to the output flow controller, wherein the control unit is configured to selectively operate the output flow controller in the first operating mode to deliver treatment solution from the plurality of treatment solution reservoirs to the treatment solution port.

2. An apparatus according to claim 1, wherein the liquid gas filter in each feeder line of the plurality of feeder lines is located closer to the treatment solution reservoir to which the feeder line is attached than the junction in the tubing set.

3. An apparatus according to claim 1, wherein the reservoir status monitor comprises at least one pressure sensor configured to measure treatment solution fluid pressure in the tubing set, and wherein the at least one pressure sensor is operably connected to the control unit.

4. An apparatus according to claim 1, wherein the reservoir status monitor comprises a sensor configured to detect treatment solution in the tubing set downstream from the empty treatment solution reservoir and upstream of the junction.

5. A method of controlling treatment solution flow in an extracorporeal blood treatment apparatus that includes a blood circuit and a treatment solution delivery system configured to deliver treatment solution within the blood treatment apparatus through a treatment solution port, wherein the treatment solution delivery system includes a plurality of treatment solution reservoirs and a tubing set that includes a junction, a plurality of feeder lines connected to the junction, and an outlet line connected to the junction, the tubing set configured to deliver treatment solution from the plurality of treatment solution reservoirs to the outlet line through the junction, the method comprising:

removing blood from a patient and returning the blood to the patient after passing the blood through a blood circuit such that the blood passes through a primary treatment chamber of a filter comprising the primary treatment chamber and a secondary chamber separated from the primary treatment chamber by a semi-permeable membrane;

delivering treatment solution from the plurality of treatment solution reservoirs to an output flow controller through the tubing set at the same time such that the plurality of treatment solution reservoirs empty simultaneously as the treatment solution is delivered to the output flow controller, wherein each treatment solution reservoir of the plurality of treatment solution reservoirs contains the same treatment solution, wherein the treatment solution from each treatment solution reservoir of the plurality of treatment solution reservoirs passes through one feeder line of the plurality of feeder lines and a liquid-gas separation filter in each feeder line of the plurality of feeder lines, wherein the liquid-gas separation filter in each feeder line is located between the treatment solution reservoir to which the feeder line is attached and the junction of the tubing set, wherein each liquid-gas separation filter comprises a hydrophilic membrane through which the treatment solution passes;

determining when at least one treatment solution reservoir of the plurality of treatment solution reservoirs requires replacement, wherein the determining comprises weighing the plurality of treatment solution reservoirs at the same time using a single gravimetric scale; and controlling operation of the output flow controller based at least in part on the determination that at least one treatment solution reservoir of the plurality of treatment solution reservoirs requires replacement.

6. A method according to claim 5, wherein the method further comprises operating the output flow controller in a reverse operating mode after replacing at least one treatment solution reservoir of the plurality of treatment solution reservoirs.

7. A method according to claim 5, wherein the liquid gas filter in each feeder line of the plurality of feeder lines is located closer to the treatment solution reservoir to which the feeder line is attached than the junction in the tubing set.

8. A method according to claim 5, wherein determining when at least one treatment solution reservoir of the plurality of treatment solution reservoirs requires replacement comprises measuring treatment solution fluid pressure in the tubing set.

9. A method according to claim 5, wherein determining when at least one treatment solution reservoir of the plurality of treatment solution reservoirs requires replacement comprises sensing treatment solution in the tubing set upstream of the junction.

10. An apparatus according to claim 1, wherein the outlet line is connected to the blood circuit through the treatment solution port.

11. A method according to claim 5, wherein the method further comprises delivering the treatment solution to the blood circuit using the output flow controller.

12. An apparatus according to claim 1, wherein the control unit is configured to operate the output flow controller in the second operating mode after replacement of at least one treatment solution reservoir of the plurality of treatment solution reservoirs.

13. An extracorporeal blood treatment apparatus comprising:

a filter comprising a primary chamber and a secondary chamber separated from the primary chamber by a semi-permeable membrane;

a blood circuit that includes an arterial line configured to deliver blood from a patient to the primary chamber and a venous line configured to remove the blood from the primary chamber and return the blood to the patient; and a treatment solution delivery system configured to deliver treatment solution within the blood treatment apparatus through a treatment solution port, wherein the treatment solution delivery system comprises:

a plurality of treatment solution reservoirs, wherein each treatment solution reservoir of the plurality of treatment solution reservoirs comprises an outlet, wherein each treatment solution reservoir of the plurality of treatment solution reservoirs contains the same treatment solution;

a tubing set comprising a junction, a plurality of feeder lines connected to the junction, and an outlet line connected to the junction, the tubing set configured to deliver treatment solution from the plurality of treatment solution reservoirs to the outlet line through the junction;

a reservoir status monitor configured to determine when a treatment solution reservoir of the plurality of treatment solution reservoirs requires replacement, wherein the reservoir status monitor comprises a gravimetric scale configured to measure the combined weight of the plurality of treatment solution reservoirs at the same time;

at least one liquid-gas separation filter positioned in the tubing set, wherein all treatment solution passing through the outlet line passes through the at least one liquid-gas separation filter, wherein each of the at least one liquid-gas separation filters comprises a hydrophilic membrane through which the treatment solution passes;

an output flow controller operatively connected to the outlet line, wherein the output flow controller is configured to deliver treatment solution from the plurality of treatment solution reservoirs to the treatment solution port, wherein the at least one liquid-gas separation filter is positioned between the plurality of treatment solution reservoirs and the output flow controller such that the plurality of treatment solution reservoirs are in simultaneous fluid communication with the at least one liquid-gas separation filter through the plurality of feeder lines of the tubing set such that the plurality of treatment solution reservoirs empty simultaneously as the treatment solution flows through the outlet line to the output flow controller, wherein each feeder line of the plurality of feeder lines is connected to one treatment solution reservoir of the plurality of treatment solution reservoirs; and a control unit operably connected to the output flow controller, wherein the control unit is configured to:
  operate the output flow controller in a forward operating mode to deliver treatment solution from the plurality of treatment solution reservoirs to the treatment solution port; and
  operate the output flow controller in a reverse operating mode causing a portion of treatment solution in the tubing set between the liquid-gas separation filter and the output flow controller to be delivered back into the tubing set between the liquid-gas separation filter and the plurality of treatment solution reservoirs;

wherein a volume of treatment solution in the plurality of feeder lines of the tubing set between the plurality of treatment solution reservoirs and the at least one liquid-gas separation filter is less than a volume of treatment solution between the at least one liquid-gas separation filter and the output flow controller.

14. An apparatus according to claim 13, wherein the control unit is configured to operate the output flow controller in the reverse operating mode after replacement of at least one treatment solution reservoir of the plurality of treatment solution reservoirs.

15. An extracorporeal blood treatment apparatus comprising:
  a filter comprising a primary chamber and a secondary chamber separated from the primary chamber by a semi-permeable membrane;
  a blood circuit that includes an arterial line configured to deliver blood from a patient to the primary chamber and a venous line configured to remove the blood from the primary chamber and return the blood to the patient; and
  a treatment solution delivery system configured to deliver treatment solution within the blood treatment apparatus through a treatment solution port, wherein the treatment solution delivery system comprises:
    a plurality of treatment solution reservoirs, wherein each treatment solution reservoir of the plurality of treatment solution reservoirs comprises an outlet, wherein each treatment solution reservoir of the plurality of treatment solution reservoirs contains the same treatment solution;
    a tubing set comprising a junction, a plurality of feeder lines connected to the junction, and an outlet line connected to the junction, the tubing set configured to deliver treatment solution from the plurality of treatment solution reservoirs to the outlet line through the junction;
    a reservoir status monitor configured to determine when a treatment solution reservoir of the plurality of treatment solution reservoirs requires replacement, the reservoir status monitor comprising a gravimetric scale configured to measure the combined weight of the plurality of treatment solution reservoirs at the same time;
    at least one liquid-gas separation filter positioned in the tubing set, wherein all treatment solution passing through the outlet line passes through the at least one liquid-gas separation filter, wherein each of the at least one liquid-gas separation filters comprises a hydrophilic membrane;
    an output flow controller operatively connected to the outlet line, wherein the output flow controller is configured to deliver treatment solution from the plurality of treatment solution reservoirs to the treatment solution port, wherein the at least one liquid-gas separation filter is positioned between the plurality of treatment solution reservoirs and the output flow controller such that the plurality of treatment solution reservoirs are in simultaneous fluid communication with the at least one liquid-gas separation filter through the plurality of feeder lines of the tubing set such that the plurality of treatment solution reservoirs empty simultaneously as the treatment solution flows through the outlet line to the output flow controller, wherein each feeder line of the plurality of feeder lines is connected to one treatment solution reservoir of the plurality of treatment solution reservoirs; and
    a control unit operably connected to the sensor and the output flow controller, wherein the control unit is configured to operate the output flow controller and wherein the sensor is configured to supply weight information to the control unit.

16. An apparatus according to claim 15, wherein the reservoir status monitor is configured to determine when a treatment solution reservoir of the plurality of treatment solution requires replacement based on the combined weight of the plurality of treatment solution reservoirs at the same time.

17. An extracorporeal blood treatment apparatus comprising:
   a filter comprising a primary chamber and a secondary chamber separated from the primary chamber by a semi-permeable membrane;
   a blood circuit that includes an arterial line configured to deliver blood from a patient to the primary chamber and a venous line configured to remove the blood from the primary chamber and return the blood to the patient; and
   a treatment solution delivery system configured to deliver treatment solution within the blood treatment apparatus through a treatment solution port, wherein the treatment solution delivery system comprises:
      a plurality of treatment solution reservoirs, wherein each treatment solution reservoir of the plurality of treatment solution reservoirs comprises an outlet, wherein each treatment solution reservoir of the plurality of treatment solution reservoirs contains the same treatment solution;
      a tubing set comprising a junction, a plurality of feeder lines connected to the junction, and an outlet line connected to the junction, the tubing set configured to deliver treatment solution from the plurality of treatment solution reservoirs to the outlet line through the junction;
      a reservoir status monitor configured to determine when a treatment solution reservoir of the plurality of treatment solution reservoirs requires replacement, wherein the reservoir status monitor comprises a gravimetric scale configured to measure the combined weight of the plurality of treatment solution reservoirs at the same time;
      at least one liquid-gas separation filter positioned in the tubing set, wherein all treatment solution passing through the outlet line passes through the at least one liquid-gas separation filter, the at least one liquid-gas separation filters being configured to pass liquid while substantially preventing the passage of gases, wherein each of the at least one liquid-gas separation filters comprises a hydrophilic membrane through which the treatment solution passes;
      an output flow controller operatively connected to the outlet line, wherein the output flow controller is configured to deliver treatment solution from the plurality of treatment solution reservoirs to the treatment solution port, wherein the at least one liquid-gas separation filter is positioned between the plurality of treatment solution reservoirs and the output flow controller such that the plurality of treatment solution reservoirs are in simultaneous fluid communication with the at least one liquid-gas separation filter through the plurality of feeder lines of the tubing set such that the plurality of treatment solution reservoirs empty simultaneously as the treatment solution flows through the outlet line to the output flow controller, wherein each feeder line of the plurality of feeder lines is connected to one treatment solution reservoir of the plurality of treatment solution reservoirs; and
      a control unit operably connected to the output flow controller, wherein the control unit is configured to operate the output flow controller;
      wherein a volume of treatment solution in the plurality of feeder lines of the tubing set between the plurality of treatment solution reservoirs and the at least one liquid-gas separation filter is less than a volume of treatment solution between the at least one liquid-gas separation filter and the output flow controller.

18. An apparatus according to claim 17, wherein the at least one liquid-gas separation filter is configured to stop fluid flow through the at least one liquid-gas separation filter if air reaches the at least one liquid-gas separation filter.

19. An apparatus according to claim 17, wherein the treatment solution delivery system further comprises, for each of the feeder lines, a connector used to connect the respective feeder line to a reservoirs, wherein each connector comprises one of the at least one liquid-gas separation filters.

20. An apparatus according to claim 17, wherein each of the at least one liquid-gas separation filter includes a hydrophilic media configured to provide a passage for liquid and/or a hydrophobic membrane configured to provide a vent for gas separated from the liquid passing the filter.

21. An apparatus according to claim 1, wherein the control unit is configured to selectively operate the output flow controller in the second operating mode to deliver a portion of treatment solution in the tubing set back into at least one treatment solution reservoir of the plurality of treatment solution reservoirs.

22. A method according to claim 5, wherein controlling operation of the output flow controller comprises:
   selectively operating the output flow controller in a forward operating mode to deliver treatment solution from the plurality of treatment solution reservoirs to the treatment solution port; and
   selectively operating the output flow controller in a reverse operating mode in which at least a portion of the treatment solution in the tubing set between the liquid-gas separation filter and the output flow controller is delivered back into the tubing set between the liquid-gas separation filter and the plurality of treatment solution reservoirs.

* * * * *